(12) United States Patent
Van Der Heide et al.

(10) Patent No.: US 10,125,071 B2
(45) Date of Patent: Nov. 13, 2018

(54) PROCESS FOR THE PRODUCTION OF GLYCOLS FROM A SACCHARIDE-CONTAINING FEEDSTOCK

(71) Applicant: SHELL OIL COMPANY, Houston, TX (US)

(72) Inventors: Evert Van Der Heide, Amsterdam (NL); Pieter Huizenga, Amsterdam (NL)

(73) Assignee: SHELL OIL COMPNAY, Houston, TX (US)

( * ) Notice: Subject to any disclaimer, the term of this patent is extended or adjusted under 35 U.S.C. 154(b) by 8 days.

(21) Appl. No.: 15/106,846

(22) PCT Filed: Dec. 19, 2014

(86) PCT No.: PCT/EP2014/078825
§ 371 (c)(1),
(2) Date: Jun. 21, 2016

(87) PCT Pub. No.: WO2015/097096
PCT Pub. Date: Jul. 2, 2015

(65) Prior Publication Data
US 2017/0001932 A1  Jan. 5, 2017

(30) Foreign Application Priority Data

Dec. 23, 2013 (EP) .................... 13199420

(51) Int. Cl.
*C07C 29/14* (2006.01)
*C07C 29/132* (2006.01)
*C07C 29/74* (2006.01)

(52) U.S. Cl.
CPC ............ *C07C 29/132* (2013.01); *C07C 29/74* (2013.01)

(58) Field of Classification Search
None
See application file for complete search history.

(56) References Cited

U.S. PATENT DOCUMENTS

| 2011/0313212 A1 | 12/2011 | Kalnes et al. |
| 2013/0165698 A1 * | 6/2013 | Powell .................... C10G 3/00 568/863 |

FOREIGN PATENT DOCUMENTS

| CN | 102643165 A | 8/2012 |
| CN | 102675045 | 9/2012 |
| WO | 2008133939 | 11/2008 |

OTHER PUBLICATIONS

Liu, Yue, et al.: Tungsten Trioxide Promoted Selective Conversion of Cellulose into Propylene Glycol and Ethylene Glycol on a Ruthenium Catalyst, Angewandte Chemie. Int. Ed. 51, pp. 3249-3253, 2012.
International Search Report dated Feb. 24, 2015 of PCT/EP2014/078825 filed Dec. 19, 2014.

* cited by examiner

Primary Examiner — Ana Z Muresan

(57) ABSTRACT

The invention provides a process for the continuous production of one or more glycols from a saccharide-containing feedstock, said process comprising the steps of: i) contacting the saccharide-containing feedstock with hydrogen in the presence of one or more catalysts in a reactor at a reaction temperature and a reaction pressure in a continuous manner, to provide a reaction effluent stream comprising hydrogen and one or more glycols; ii) separating hydrogen from the reaction effluent stream, without substantial de-pressurization of said reaction effluent stream to provide a separated hydrogen stream and a liquid effluent stream; and iii) providing at least a portion of the separated hydrogen stream as a hydrogen recycle stream to the reactor for re-use in step i).

9 Claims, 2 Drawing Sheets

PROCESS FOR THE PRODUCTION OF GLYCOLS FROM A SACCHARIDE-CONTAINING FEEDSTOCK

PRIORITY CLAIM

The present application is a National Stage (§ 371) application of PCT/EP2014/078825, filed 19 Dec. 2014, which claims priority from European Application 13199420.4 filed 23 Dec. 2013, each of which are hereby incorporated by reference in their entirety.

FIELD OF THE INVENTION

The present invention relates to a process for the production of glycols from a saccharide-containing feedstock.

BACKGROUND OF THE INVENTION

In recent years increasing efforts have been focussed on reducing the reliance on fossil fuels as a primary resource for the provision of fuels and commodity chemicals. Carbohydrates and related 'biomass' are seen as key renewable resources in the efforts to provide new fuels and alternative routes to desirable chemicals.

In particular, certain carbohydrates can be reacted with hydrogen in the presence of a catalyst system to generate polyols and sugar alcohols, such as glycols. An example of such a process is described in Angew. Chemie. Int. Ed. 2012, 51, 3249 and US 2011/0313212 and may be used to provide ethylene glycol and 1,2-propylene glycol, which are valuable materials with a multitude of commercial applications, e.g. as heat transfer media, antifreeze, and precursors to polymers, such as PET. Ethylene and 1,2-propylene glycols are traditionally made on an industrial scale by hydrolysis of the corresponding alkylene oxides, which are the oxidation products of ethylene and propylene, produced from fossil fuels.

The conversion of carbohydrates to polyols and sugar alcohols may be carried out in a batch or semi-batch process in the art. In the processes described in CN 102675045, reactants are added to the reactor and it is heated and pressurised. After the reaction is complete, the reactor is cooled and de-pressurised before the desired products can be recovered.

US 2011/0303212 describes a continuous process for generating polyols from a cellulose-containing feedstock. In this process, hydrogen, water, catalyst and co-products are all separately recovered and recycled. The recycled hydrogen requires re-pressurisation before being fed back to the reactor.

A considerable amount of energy is required by prior art processes in order to heat and pressurise the reactor and to provide suitable conditions for the conversion of saccharides into polyols. This energy is often lost or used inefficiently during product recovery.

There remains a requirement for a continuous process for the conversion of saccharides into polyols, especially glycols, in which the energy present in the reactor effluent stream is preserved and efficiently re-integrated into the process.

SUMMARY OF THE INVENTION

Accordingly, the present invention provides a process for the continuous production of one or more glycols from a saccharide-containing feedstock, said process comprising the steps of:

i) contacting the saccharide-containing feedstock with hydrogen in the presence of one or more catalysts in a reactor at a reaction temperature and a reaction pressure in a continuous manner to provide a reaction effluent stream comprising hydrogen and one or more glycols;

ii) separating hydrogen from the reaction effluent stream, without substantial de-pressurisation of said reaction effluent stream to provide a separated hydrogen stream and a liquid effluent stream; and iii) providing at least a portion of the separated hydrogen stream as a hydrogen recycle stream to the reactor for re-use in step i).

DETAILED DESCRIPTION OF THE INVENTION

Figure 1:
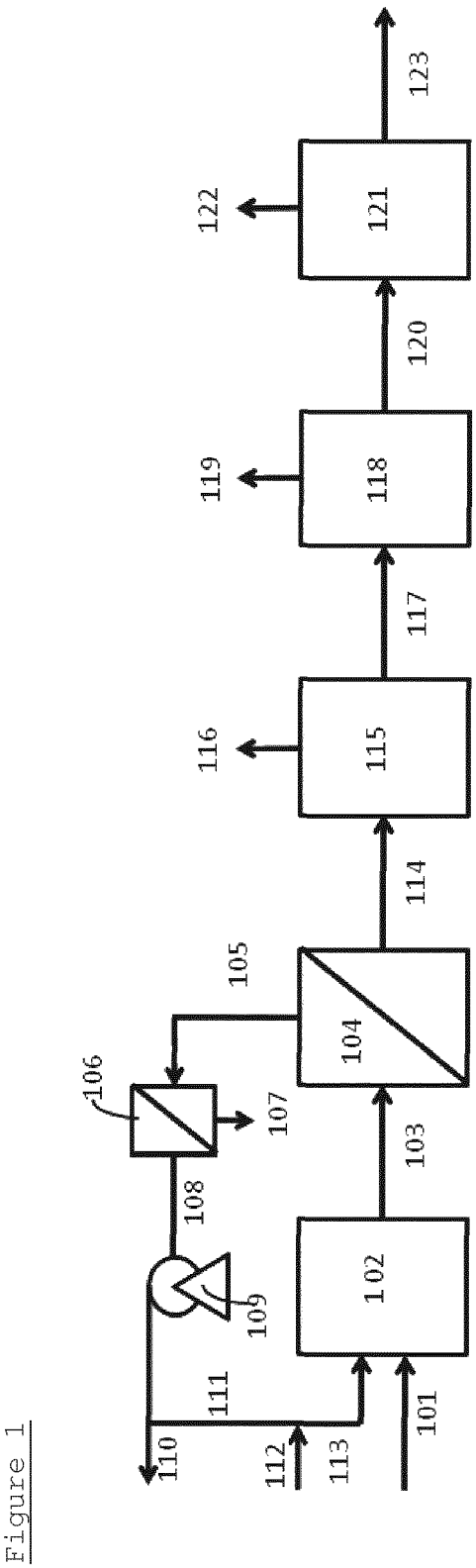
FIGS. 1 and 2 are schematic diagrams showing aspects of exemplary, but non-limiting, embodiments of the process described herein.

The present invention allows recycling of the hydrogen present in the reaction effluent stream from a reaction to produce glycols from a saccharide-containing feedstock, without the need for significant re-pressurisation. This process eliminates inefficiencies in the overall process. Further improvements to the process may be achieved by efficiently integrating the energy present in the reaction effluent stream into other sections of the process, such as the product recovery section.

The process requires a saccharide-containing feedstock. Said feedstock suitably comprises at least 1 wt % saccharide in a solvent. Preferably the saccharide-containing feedstock comprises at least 2 wt %, more preferably at least 5 wt %, even more preferably at least 10 wt %, most preferably at least 20 wt % saccharide in a solvent. Suitably, the saccharide-containing feedstock contains no more than 50 wt %, preferably no more than 40 wt % saccharide in a solvent.

One or more further feed streams comprising solvent may also be added to the reactor together with the saccharide-containing feedstock, either through the same feed pipe or at a separate point in the reactor.

It is envisaged that the composition and amount of the saccharide-containing feedstock, the contents of the reactor and the amount of any further feed stream added to the reactor will be coordinated such that the concentration of saccharide in the solvent in the reactor while the reaction is proceeding is at least 0.01 wt % saccharide in solvent. Preferably the concentration of saccharide in solvent in the reactor is at least 0.02 wt %. Most preferably the concentration of saccharide in solvent in the reactor is at least 0.25 wt %. It is envisaged that the composition and amount of the saccharide-containing feedstock, the contents of the reactor and the amount of any further feed stream added to the reactor will be coordinated such that the concentration of saccharide in the solvent in the reactor while the reaction is proceeding is at most 5 wt % saccharide in solvent. Preferably the concentration of saccharide in solvent in the reactor is at most 2 wt %. Most preferably the concentration of saccharide in solvent in the reactor is at most 1.5 wt %.

The saccharide-containing feedstock comprises at least one saccharide selected from the group consisting of monosaccharides, disaccharides, oligosaccharides and polysaccharides. Examples of polysaccharides include cellulose, hemicelluloses, starch, glycogen, chitin and mixtures thereof. If the saccharide-containing feedstock comprises oligosaccharides or polysaccharides, it is preferable that it is subjected to pre-treatment before being fed to the reactor in a form that can be converted to glycols when contacted with hydrogen in the reactor in the presence of a suitable catalyst system. Suitable pre-treatment methods are known in the art and one or more may be selected from the group including, but not limited to, sizing, drying, grinding, hot water treatment, steam treatment, hydrolysis, pyrolysis, thermal treatment, chemical treatment, biological treatment.

Preferably, the saccharide-containing feedstock that is fed to the reactor, after pre-treatment if necessary, comprises one or more saccharide selected from the group consisting of glucose, sucrose and starch. Said saccharide is suitably present as a solution, a suspension or a slurry in the solvent.

The solvent may be water, a $C_1$ to $C_6$ alcohol, or mixtures thereof. Preferably, the solvent is water. As well as the solvent provided in the saccharide-containing feedstock there may also be further solvent already present in the reactor and/or added to the saccharide-containing feedstock as set out above. Said solvent is also suitably water, a $C_1$ to $C_6$ alcohol, or mixtures thereof. Preferably, all solvents are the same. More preferably, all solvents comprise water. Most preferably, all solvents are water.

The temperature in the reactor, referred to herein as the reaction temperature, is suitably at least 130° C., preferably at least 150° C., more preferably at least 170° C., most preferably at least 190° C. The temperature in the reactor is suitably at most 300° C., preferably at most 280° C., more preferably at most 270° C., even more preferably at most 250° C. Preferably, the temperature in the reactor is above the degradation temperature of the one or more saccharides in the saccharide feedstock. Preferably, the reactor is heated to a temperature within these limits before addition of any starting material and is maintained at such a temperature until all reaction is complete.

The pressure in the reactor, referred to herein as the reaction pressure, must be above the vapour pressure of the solvent at the reaction temperature and is suitable at least 1 MPa, preferably at least 2 MPa, more preferably at least 3 MPa. The pressure in the reactor is suitably at most 16 MPa, preferably at most 12 MPa, more preferably at most 10 MPa, even more preferably at most 8 MPa, most preferably at most 6 MPa. Preferably, the reactor is pressurised to a pressure within these limits by addition of hydrogen before addition of any saccharide-containing feedstock. The pressure of hydrogen is maintained by addition of hydrogen throughout the process.

The process of the invention is carried out in a continuous manner, that is reactants are supplied continuously to the reactor and a reaction effluent stream is removed continuously from the reactor while the reaction is proceeding.

The reactor referred to herein may comprise a single reactor vessel or multiple reactor vessels connected in series or parallel.

Any reactor type or combination of reactors suitable for a continuous flow process in which reaction product is continuously removed from the reactor as a reaction effluent stream may be used for the process of the present invention. For example, suitable reactor systems include ebullated catalyst bed reactor systems, immobilized catalyst reactor systems having catalyst channels, augured reactor systems, tubular reactors, fluidized bed reactor systems, mechanically mixed reactor systems and slurry reactor systems, also known as a three phase bubble column reactor systems, and combinations thereof.

The process of the present invention takes place in the presence of hydrogen. Preferably, the process of the present reaction takes place in the absence of air or oxygen. In order to achieve this, it is preferable that the atmosphere in the reactor be evacuated and replaced with hydrogen repeatedly, after loading of any initial reactor contents, before the reaction starts. Preferably, the continuous production of one or more glycols from a saccharide-containing feedstock comprises the conversion of one or more saccharides in the presence of hydrogen and one or more catalysts to ethylene glycol and 1,2-propylene glycol. In this embodiment of the invention, the one or more catalysts used preferably comprises at least two active catalytic components comprising, as a first active catalyst component, one or more materials selected from transition metals from groups 8, 9 or 10 or compounds thereof, with catalytic hydrogenation capabilities; and, as a second active catalyst component, one or more materials selected from tungsten, molybdenum and compounds and complexes thereof.

Preferably, the first active catalyst component consists of one or more of the group selected from iron, cobalt, nickel, ruthenium, rhodium, palladium, iridium and platinum. This component may be present in the elemental form or as a compound. It is also suitable that this component is present in chemical combination with one or more other ingredients in the catalyst system. It is required that the first active catalyst component has catalytic hydrogenation capabilities and it is capable of catalysing the hydrogenation of material present in the reactor.

Preferably, the second active catalyst component comprises of one or more compound, complex or elemental material comprising tungsten, molybdenum, vanadium, niobium, chromium, titanium or zirconium. More preferably the second active catalyst component comprises one or more material selected from the list consisting of tungstic acid, molybedic acid, ammonium tungstate, ammonium metatungstate, ammonium paratungstate, tungstate compounds comprising at least one Group I or II element, metatungstate compounds comprising at least one Group I or II element, paratungstate compounds comprising at least one Group I or II element, heteropoly compounds of tungsten, heteropoly compounds of molybdenum, tungsten oxides, molybdenum oxides, vanadium oxides, metavanadates, chromium oxides, chromium sulfate, titanium ethoxide, zirconium acetate, zirconium carbonate, zirconium hydroxide, niobium oxides, niobium ethoxide, and combinations thereof. The metal component is in a form other than a carbide, nitride, or phosphide. Preferably, the second active catalyst component comprises one or more compound, complex or elemental material selected from those containing tungsten or molybdenum.

The catalyst components may be heterogeneous or homogeneous with respect to the solvent or solvents present in the reactor during the process of the present invention. The catalyst components may be preloaded into the reactor or, if they are in liquid form or present as a solution or slurry in a solvent, they may be fed into the reactor as required in a continuous or discontinuous manner during the process of the present invention.

Preferably, at least one of the active catalyst components is supported on a solid support. In this embodiment, any other active catalyst component may be present in either heterogeneous or homogeneous form. Said any other active catalyst component may also be supported on a solid support. In one embodiment, the first active catalyst component is supported on one solid support and the second active catalyst component is supported on a second solid support which may comprise the same or different material. In another embodiment, both active catalyst components are supported on one solid support.

The solid supports may be in the form of a powder or in the form of regular or irregular shapes such as spheres, extrudates, pills, pellets, tablets, monolithic structures. Alternatively, the solid supports may be present as surface coatings, for examples on the surfaces of tubes or heat exchangers. Suitable solid support materials are those known to the skilled person and include, but are not limited to aluminas, silicas, zirconium oxide, magnesium oxide, zinc oxide, titanium oxide, carbon, activated carbon, zeolites, clays, silica alumina and mixtures thereof.

Suitably, the weight ratio of the first active catalyst component to the second active catalyst component is in the range of from 0.02:1 to 3000:1, preferably in the range of from 0.1:1 to 100:1, on the basis of the weight of metal present in each component.

The weight ratio of the first active catalyst component (based on the amount of metal in said component) to sugar is suitably in the range of from 1:100 to 1:10000. The weight ratio of the second active catalyst component (based on the amount of metal in said component) to sugar is suitably in the range of from 1:10 to 1:1000.

In step ii) of the process, a reaction effluent stream is removed from the reactor. As indicated previously, it is removed continuously as the reaction progresses. The reaction effluent stream comprises hydrogen and one or more glycols. The reaction effluent stream preferably also comprises solvent. The reaction effluent stream may also contain unreacted saccharide, intermediates, by-products and catalyst materials. Said catalyst materials may be the result of decomposition of the catalyst system in the reactor or may be catalyst material present as part of an at least partially homogeneous catalyst system.

Any solid material such as catalyst materials may be removed from the reaction effluent stream by means of filtration. Preferably, the separation takes place inside the reactor vessel, for example by filtration. Alternatively, the catalyst materials may be separated downstream of the reactor vessel and then recycled to the reactor or a reactor feed stream.

Hydrogen is separated from the reaction effluent stream, suitably by means of a gas/liquid separator, to provide a separated hydrogen stream and a liquid effluent stream. Said gas/liquid separator may be inside of or downstream of the reactor. The hydrogen is separated without substantial de-pressurisation of said reaction effluent stream. As used herein, 'without substantial de-pressurisation of said reaction effluent stream' means that the reaction effluent stream is substantially at the same pressure at which the reaction is carried out. Preferably, the reaction effluent stream is at the same pressure at which the reaction is carried out. It will be readily understood that some slight de-pressurisation may occur when removing the reaction effluent stream from the reactor. Therefore, 'substantially at the same pressure at which the reaction is carried out' can be considered to be within 0.2 MPa, preferably within 0.1 MPa, more preferably within 0.05 MPa, even more preferably within 0.02 MPa, most preferably within 0.01 MPa of the reaction pressure.

Preferably, the hydrogen is also separated without substantial loss in temperature of said reaction effluent stream. As used herein, 'without substantial loss in temperature of said reaction effluent stream' means that the reaction effluent stream is substantially at the same temperature at which the reaction is carried out. Preferably, the reaction effluent stream is at the same temperature at which the reaction is carried out. It will be readily understood that some slight loss in temperature may occur when removing the reaction effluent stream from the reactor. Therefore, 'substantially at the same temperature at which the reaction is carried out' can be considered to be within 20° C., preferably within 10° C., more preferably within 5° C., most preferably within 2° C. of the reaction temperature.

After being separated from the reaction effluent stream, at least a portion, preferably substantially all, more preferably all of the separated hydrogen stream is recycled as a hydrogen recycle stream to the reactor for re-use.

Optionally, before being recycled to the reactor, the separated hydrogen stream may be cooled in order to remove condensibles.

Also optionally, a bleed stream may be taken from the separated hydrogen stream in order to prevent build up of inerts in the overall process.

It is envisaged that the separated hydrogen stream or the hydrogen recycle stream may be subjected to a minor amount of compression before being recycled to the reactor in order to move the hydrogen and also in order to make up for any slight de-pressurisation that may have occurred.

Preferably, a hydrogen make up stream is also provided to the process, either directly to the reactor or into the hydrogen recycle stream in order to make up for hydrogen used in the reaction or lost elsewhere.

The remaining liquid effluent stream will then require separation and purification of the desired products. Unreacted saccharides and intermediates may be separated and recycled to the saccharide-containing feedstock.

Preferably the remaining liquid effluent stream is cooled down by staged flashing, which removes solvent (e.g. water) from the liquid effluent stream as vapour. The energy contained in this evaporated solvent may then be used elsewhere in the process in order to provide heat integration and energy efficiencies.

In a preferred embodiment of the invention, this heat may be integrated by using it in a multi-stage evaporation of the solvent, wherein a first evaporation stage is carried out at a certain temperature and pressure and the vapour (steam) produced is then used to provide heat to the second evaporation stage which is operated at a lower temperature and pressure. The vapour produced in the second stage is then used in the third stage and so on. Each stage operates at a lower temperature and pressure, optionally down to vacuum conditions, than the previous stage.

After removal of the solvent, the desired glycols may be purified by any suitable method including, but not limited to, distillation, extraction and the like.

Embodiments of the present invention will now be described by way of example only and with reference to the accompanying non-limiting figures.

In FIG. 1, a saccharide-containing feedstock stream 101 is fed to a reactor 102, where it is contacted with hydrogen in the presence of one or more catalysts at a reaction temperature and reaction pressure. A reaction effluent stream 103 is removed from the reactor and hydrogen is separated in a gas/liquid separator 104, without substantial de-pressurisation of the reaction effluent stream, to provide a separated hydrogen stream 105 and a first liquid effluent stream 114.

Condensibles 107 may be removed from the separated hydrogen stream 105 after cooling in a second gas/liquid separator 106. The resultant stream 108 may be subjected to slight compression in a gas compressor 109. Optionally a bleed stream 110 is removed and the remaining hydrogen recycle stream 111 is combined with a hydrogen make-up stream 112 in order to provide the hydrogen feed stream 113 for the reactor 102.

The first liquid effluent stream 114 is passed to a first evaporator 115 to provide a first vapour stream 116 and a second liquid effluent stream 117. This second liquid effluent stream 117 is then passed to a second evaporator 118 to provide a second vapour stream 119 and a third liquid effluent stream 120. This third liquid effluent stream 120 is then passed to a third evaporator 121 to provide a third vapour stream 122 and a third liquid effluent stream 123. The third liquid effluent stream is then subjected to further purification in order to obtain the desired glycol products. The energy contained in vapour streams 116, 119 and 122 as heat may be used as a heat source for other parts of the process.

Figure 2:
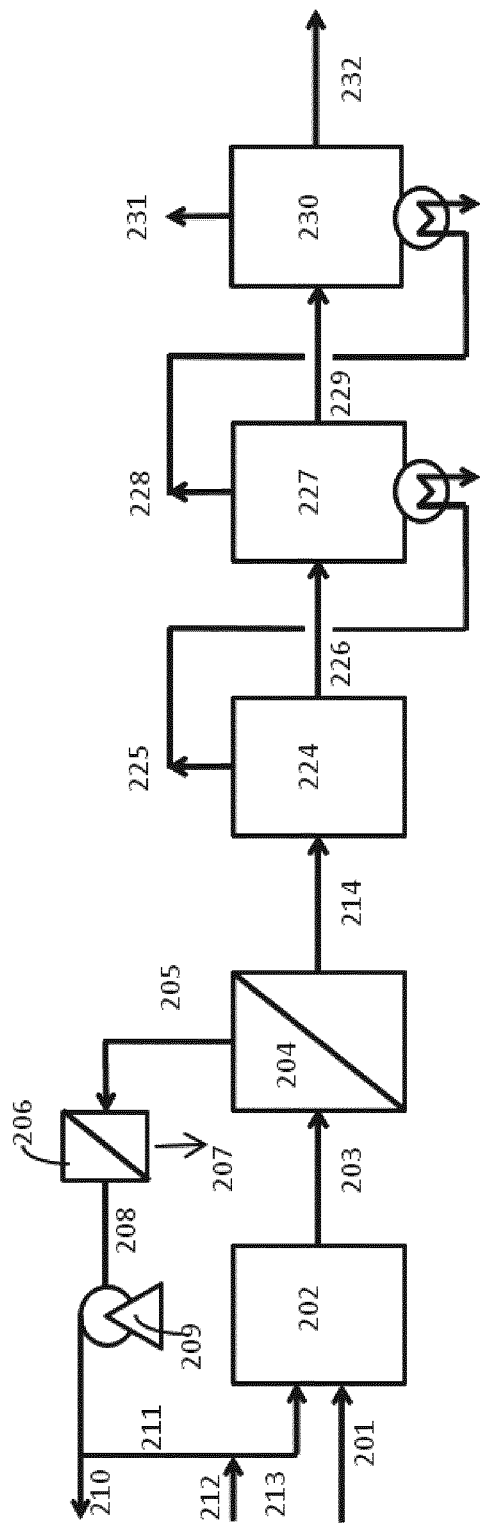

A further embodiment of the invention is shown in FIG. 2. In this figure, the same reference numerals are used to refer to the same features as in FIG. 1, but with the prefix of 2 (for FIG. 2) instead of 1 (for FIG. 1) For example, the reactor is labelled 102 in FIGS. 1 and 202 in FIG. 2.

In FIG. 2, the same process occurs providing hydrogen recycle and a first liquid effluent stream 214. In this embodiment, the first liquid effluent stream 214 is fed to a first evaporation stage 224 in a multi-effect evaporator. In the first evaporation stage 224, a first vapour stream 225 and a second liquid effluent stream 226 are produced. The second liquid effluent stream is fed to a second evaporation stage 227, wherein in heat is provided by the first vapour stream 225. In the second evaporation stage 227, a second vapour stream 228 and a third liquid effluent stream 229 are produced. The third liquid effluent stream is fed to a third evaporation stage 230, wherein in heat is provided by the second vapour stream 228. In the third evaporation stage 230, a third vapour stream 231 and a third liquid effluent stream 232 are produced. It will be readily envisaged that more or less than 3 evaporation stages may be used in such a process. The final vapour stream may be used to provide heat to another part of the process. The final liquid effluent stream will be subjected to further purification in order to obtain the desired glycol products.

The invention claimed is:

1. A process for the continuous production of one or more glycols from a saccharide-containing feedstock, said process comprising the steps of:
   i) contacting the saccharide-containing feedstock with hydrogen in the presence of one or more catalysts in a reactor at a reaction temperature and a reaction pressure in a continuous manner, to provide a reaction effluent stream comprising hydrogen and one or more glycols;
   ii) separating hydrogen from the reaction effluent stream, to provide a separated hydrogen stream and a first liquid effluent stream, wherein the hydrogen is separated from the reaction effluent stream at a pressure within 0.2 MPa of the reaction pressure;
   iii) providing at least a portion of the separated hydrogen stream as a hydrogen recycle stream to the reactor for re-use in step i); and
   iv) cooling the first liquid effluent stream to provide a second effluent stream and a first vapour stream, wherein the first vapour stream provides heat to the process; wherein the reaction temperature is in the range of from at least 130° C. to at most 300° C. and the reaction pressure is in the range of from at least 1 MPa to at most 16 MPa.

2. The process according to claim 1, wherein the saccharide-containing feedstock comprises at least 1 wt % saccharide in a solvent.

3. The process according to claim 2, wherein the solvent is water.

4. The process according to claim 1, wherein the saccharide-containing feedstock comprises oligosaccharides and/or polysaccharides and is subjected to a pre-treatment step before being fed to the reactor.

5. The process according to claim 1, wherein the saccharide-containing feedstock fed to the reactor comprises one or more saccharides selected from the group consisting of glucose, sucrose and starch.

6. The process according to claim 1, wherein the hydrogen is separated from the reaction effluent stream at a pressure within 0.1 MPa of the reaction pressure.

7. The process according to claim 1, wherein cooling the first liquid effluent stream is by staged flashing.

8. The process according to claim 2, wherein cooling the first liquid effluent stream is by multistage evaporation of the solvent.

9. The process according to claim 1, wherein the hydrogen is separated from the reaction effluent stream at a temperature within 20° C. of the reaction temperature.

* * * * *